United States Patent [19]

Moayeri

[11] Patent Number: 5,728,939
[45] Date of Patent: Mar. 17, 1998

[54] PROBE, DEVICE AND METHOD FOR TESTING EGGS

[75] Inventor: Hossein Moayeri, Soest, Netherlands

[73] Assignee: FPS Food Processing Systems B.V., Netherlands

[21] Appl. No.: 632,062

[22] Filed: Apr. 15, 1996

[30] Foreign Application Priority Data

Apr. 19, 1995 [NL] Netherlands ............... 1000177

[51] Int. Cl.$^6$ ............... G01M 7/00; G01H 1/00
[52] U.S. Cl. ............... 73/595; 73/579
[58] Field of Search ............... 356/52, 57, 58, 356/67, 53, 55; 15/153.1; 73/595, 579, 12, 79, 668

[56] References Cited

U.S. PATENT DOCUMENTS 3,503,501  3/1970  Seaborn ............... 209/111.9

FOREIGN PATENT DOCUMENTS 0 295 755  12/1988  European Pat. Off. .
6814933  4/1969  Netherlands .

OTHER PUBLICATIONS

Patent Abstracts of Japan, vol. 10, No. 380 (P528) [2437], 19 Dec. 1986, & JP,A,61 169761 (Taisei Corp), 31 Jul. 1986.

Patent Abstracts of Japan, vol. 10, No. 140 (P–458) [2197], 23 May 1986, & JP,A,60 259955 (Chishitsu Keisoku K.K., 23 Dec. 1985.

*Primary Examiner*—Frank G. Font
*Assistant Examiner*—Michael P. Stafira
*Attorney, Agent, or Firm*—Larson and Taylor

[57] ABSTRACT

A probe for an egg-testing device includes a probe tube with an annular magnet disposed at a bottom end thereof. In the probe tube, a spherical excitation member is magnetically retained by the annular magnet. The probe is axially movable in a metal tube around which a bobbin is wound. In a rest position, the probe is retained by the magnetic attractive force between the metal tube and the annular magnet. The probe is brought into an operating position by an excitation pulse supplied to the bobbin, which pulse is provided by a control unit, taking into account the diameter of an egg to be tested and the conveying speed of a conveyor.

23 Claims, 4 Drawing Sheets

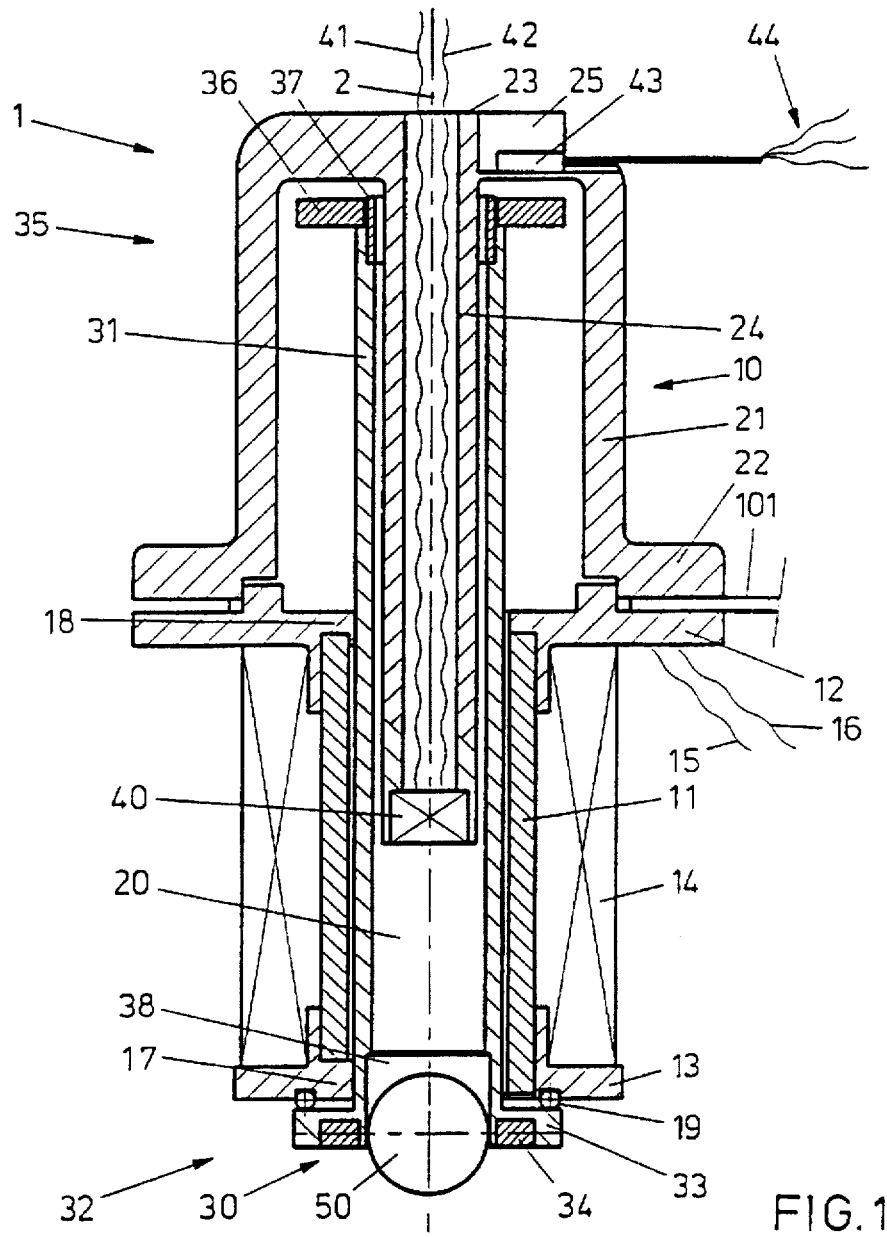
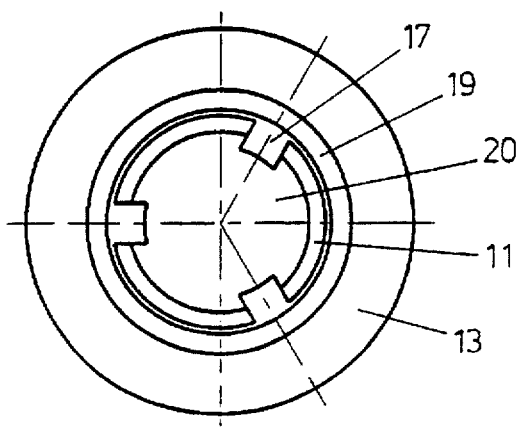
FIG.1
FIG.2

5,728,939

PROBE, DEVICE AND METHOD FOR TESTING EGGS

FIELD OF THE INVENTION

The invention relates to a probe for testing an egg for the presence of cracks or other defects.

BACKGROUND OF THE INVENTION

For testing an egg for the presence of cracks, ruptures or other defects, it is known to excite that egg with a pulse-shaped mechanical point load, whereby the eggshell is set vibrating. The vibration characteristic of the eggshell is indicative of the presence of a defect within a predetermined distance relative to the excitation position. In Europen patent specification 0,602,285, the excitation is effected by an excitation member which is suspended by means of a diaphragm at an end of a tube. Mounted at the other end of the tube is a microphone for receiving sound waves in the tube caused by the excitation member. In this known device, the excitation member is a spherical body. The tube is axially displaceable to enable the excitation member to be brought into contact with an egg to be examined. The displacement of that tube takes place by means of a stepping motor which, via two drive wheels, engages a drive rod attached to that tube.

Although this construction is in itself satisfactory, there are nevertheless some problems attached to it.

An important problem relates to the attachment of the spherical excitation member by means of a diaphragm in the tube. Such an attachment is quite difficult to manufacture. Attaching by means of glueing is a complicated procedure, and the necessity of using glue is experienced as undesired.

A further important problem concerns the relatively short life of the diaphragm.

Further, it has proven rather difficult to give the probe reproducible characteristics, since it is particularly difficult to bring the thickness of the diaphragm to the proper value. This is a drawback, on the one hand because, in practice, a large number of such probes will be used in a testing apparatus, and on the other hand because after replacement of a specific specimen by another specimen, the response of the new specimen is not simply comparable with the old specimen. In practice, the replacement of specimens is an operation which occurs relatively often, because the device is easily fouled by broken eggs, which necessitates cleaning.

In itself, the cleaning of the individual devices is a problem as well, precisely because of the attachment of the excitation member by means of a diaphragm.

A further problem of the known construction concerns the attachment of the microphone to the top end of the tube. In the first place, this has as a consequence that the weight of the moving parts of the known construction is relatively great. In the second place, it is a problem to transmit the signals from the moving microphone to a signal-processing device: it is true that for this purpose it is possible to utilize an electrically conductive wire which is free over some distance thereof, enabling it to follow the reciprocation of the microphone, but that wire may nevertheless impede the movement of the probe, while during the exchange of probes (for instance for cleaning purposes), having to detach the wire and attach it again is troublesome. In the third place, it is possible that the microphone attached to the tube does not only receive the sound waves caused by the excitation member, but also vibrations of the tube itself, which is undesired.

In this connection, it also matters that the drive by means of a motor may introduce undesired vibrations. Via the drive rod, those vibrations will be transmitted almost directly to the microphone. A further drawback of the known drive is that the use of a motor requires quite some space and a relatively complicated control, and is relatively expensive.

SUMMARY OF THE INVENTION

A general object of the present invention is to provide improved equipment for testing eggs.

An important object of the present invention is to solve the above-mentioned problems.

In accordance with an important aspect of the present invention, a probe utilizes a magnetic field as retaining means for the excitation member. The retaining means may, for example, be a ring magnet and the excitation member may be manufactured from a magnetically attractable material.

Because the excitation member is contactlessly suspended in the tube by means of a magnetic field, with a narrow air gap between the inner wall of the tube and the excitation body, a particularly good reproducibility is realized with relatively simple means. Removal and repositing of the excitation member, for instance for cleaning purposes, can be performed in a very simple manner by means of an implement which is magnetic itself, such as for instance a permanent magnet held in hand.

It is possible that the magnetic field is provided by a magnet coil. However, it is preferred to use a permanent magnet therefor, because it contributes to the reproducibility.

It is conceivable that the excitation member is manufactured from a permanent magnet. However, it is preferred that the permanent magnet be fixedly disposed adjacent the end of the tube, and that the excitation member be manufactured from a magnetically attractable and preferably stainless material. A shape which offers good results is a spherical excitation member. Some permanent magnets of a suitable shape can be disposed along the circumference of the tube. Preferably, an annular magnet is utilized.

The combination of an annular magnet and a stainless steel spherical excitation member is also preferred because they are manufactured as standard articles with good reproducibility and are commercially available.

In accordance with another aspect of the present invention, the microphone is fixedly disposed, i.e. free of the moving tubular probe body.

In accordance with a further aspect of the present invention, for establishing the reciprocation of the probe body, a switchable electromagnet is utilized, so that no motor drive is required.

BRIEF DESCRIPTION OF THE DRAWINGS

These and other aspects, characteristics and advantages of the present invention will be explained by the following description of a preferred embodiment of an egg-testing device according to the invention, with reference to the accompanying drawings, wherein:

FIG. 1 shows a longitudinal section of an egg-testing device with a probe according to the invention;

FIG. 2 is a bottom view of the egg-testing device of FIG. 1, with a probe taken away;

DETAILED DESCRIPTION OF THE PREFERRED EMBODIMENTS

Figure 3:
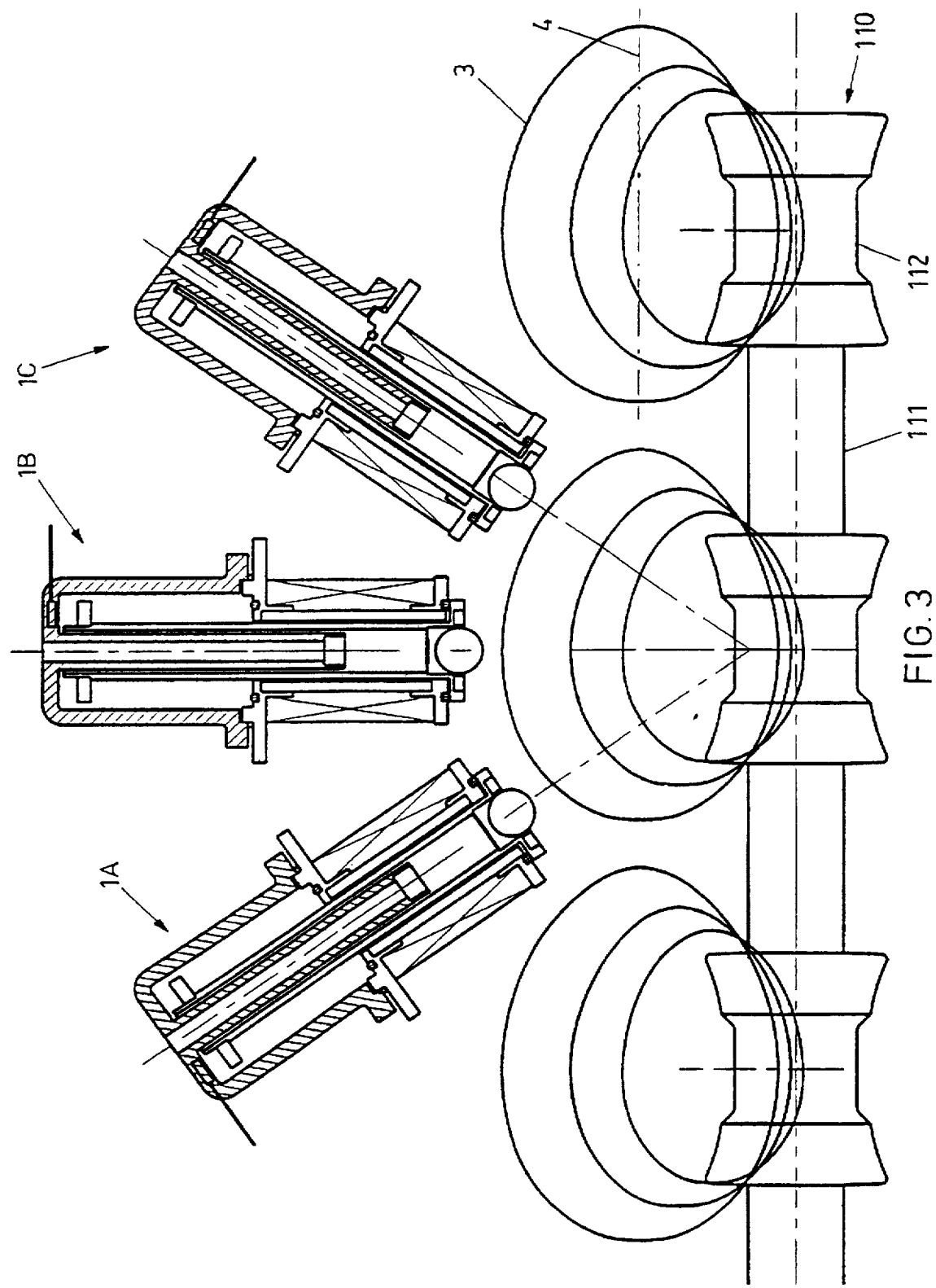
FIG. 3 is a diagrammatic view in the longitudinal direction of a roller conveyor of an egg-testing device.

In FIG. 1, an egg-testing device is generally designated by reference numeral 1. The egg-testing device 1 comprises a housing 10 intended to be fixedly mounted on a subframe 101 of an egg-testing device, as will be discussed hereinafter.

The housing 10 comprises a tube 11 of a magnetizable material, such as ferromagnetic stainless steel or nickel-plated steel. Attached to the tube 11 at a first end thereof is a fastening flange 12 serving for attachment to the subframe. The fastening flange 12 is advantageously made from synthetic material. Attached at the other end of the tube 11 is a second flange 13, which is also advantageously made from synthetic material. Between the two flanges 12 and 13, a bobbin 14 is wound on the tube 11. The bobbin 14 can be formed by several windings of a single wire, whose ends 15 and 16 are designed for external connection.

In the tube 11, a probe 30 is disposed. The probe 30 comprises a hollow, tubular probe body 31, hereinafter referred to as probe tube, having an outside contour which is adapted to the inside contour of the tube 11 but which has slightly smaller cross dimensions, so that the probe tube 31 is axially freely movable in the tube 11. The axial length of the probe tube 31 is greater than the axial length of the tube 11, with the difference between the axial length of the probe tube 31 and the axial length of the tube 11 defining a free stroke for the probe tube 31.

Advantageously, the tube 11 has a circular cross section, just as the probe tube 31, as appears more clearly from FIG. 2. In this FIG. 2, wherein the probe tube 31 is left out, it is also clearly visible that the second flange 13 may comprise a number of guide projections 17 (in the example shown: three), projecting radially inwards from the inner wall of the tube 11 to prevent the probe tube 31 from touching the inner wall of the tube 11. Comparable guide projections 18 may be formed on the fastening flange 12.

During operation, the probe tube 31 is coaxially disposed within the tube 11, their common center line 2 being substantially vertically oriented. At a bottom end 32 of the probe tube 31, a probe flange 33 is formed on the probe tube 31, in which flange an annular, axially polarized magnet 34 is mounted, for instance through glueing or clamping it in an annular groove in the probe flange 33. Such annular magnets are commercially available with a proper reproducibility. Preferably, the annular magnet 34 has its north pole directed towards the tube 11, for a reason that will be explained later on.

Advantageously, the probe tube 31 and the probe flange are manufactured as one whole from plastic.

Mounted at the top end 35 of the probe tube 31 is a stop flange 36. This stop flange 36 is preferably formed by a second annular magnet, while from a viewpoint of manufacture it is advantageous if the second annular magnet 36 is identical to the first annular magnet 34. In the example shown, the attachment of the second annular magnet 36 to the probe tube 31 is effected by means of a metal coupling bush 37, fixed to the top end 35 of the probe tube 31 by means of, for instance, glueing. The metal coupling bush 37 has an outside diameter which is only slightly less than the inside diameter of the second annular magnet 36, so that the second annular magnet 36 fits around the metal coupling bush 37. In that position, the second annular magnet 36 is magnetically attracted by the metal coupling bush 37 and held in position, and the attractive force exerted is sufficient to enable a reliable use. On the other hand, the second annular magnet 36 acting as stop flange can readily be manually removed from the probe tube 31 through exertion of a pulling force which overcomes the above-mentioned attractive force.

Provided at the bottom end 32 of the probe tube 31 is a magnetically attractable excitation member 50. In the example shown, the magnetically attractable excitation member 50 is spherical, and it is manufactured from a stainless steel or nickel-plated steel. A diameter that was found suitable for the excitation member 50 is about 9 mm.

Alternatively, the excitation member 50 may have a cylindrical shape, whilst the bottom end may taper off and have a rounded tip. However, the use of the spherical shape illustrated is preferred, because during excitation, a cylindrical excitation member could tilt and then touch the inside of the tube 11 in an undefined manner, which is disadvantageous to the sound signal generated. The main aspect is that the excitation member 50 is contactlessly suspended within the probe tube 31 by a magnetic field, and is free to vibrate in the direction of the center line 2 of the probe tube 31, i.e. vertically. For that purpose, at least adjacent the bottom end 32, the diameter of the probe tube 31 is slightly greater than the diameter of the excitation member 50. A value that was found suitable for the width of the gap between the excitation member 50 and the inner wall of the probe tube 31 is 0.1–0.2 mm.

The probe tube 31 need not have a greater diameter than the excitation member 50 throughout its length. In the embodiment shown, the probe tube 31 generally has an inside diameter smaller than the diameter of the excitation member 50, and only from the bottom end 32 of the probe tube 31, a vibration chamber 38 for the excitation member 50 is defined by a probe tube portion of a greater diameter. The height of the vibration chamber 38 can be of the order of the diameter of the spherical excitation member 50. If the excitation member 50 has a shape other than spherical, for instance a cylindrical shape, then the height of the vibration chamber 38 should be selected so that the excitation member 50 can be withdrawn into the probe tube 31 as a whole.

FIG. 1 shows the egg-testing device 1 in a rest state, wherein the probe tube 31 is retracted into the housing 10 and the probe 30 is in its highest position, with the probe flange 33 abutting against the second flange 13. In this highest position, the probe 30 is retained through the attractive force between the annular magnet 34 and the tube 11. The bobbin 14 is currentless.

When the egg-testing device 1 is to be used for testing an egg, a current pulse (or voltage pulse) of a first polarity is supplied, which first polarity is such that the magnetic field generated by the bobbin 14 exerts a repulsive force on the annular magnet 34. In the example mentioned, the first polarity is such that the bobbin 14 acquires a north pole directed towards the annular magnet 34. The downwardly directed force exerted on the probe 30 by the magnetic field generated should be sufficiently great to overcome the attractive force between the annular magnet 34 and the tube 11. Under the influence of gravitational force, the probe 30 then falls down further.

If no egg is located under the egg-testing device 1, the probe 30 will reach a lowest position wherein the stop flange 36 abuts against a top face of the fastening flange 12.

The probe 30 can be returned by re-exciting the bobbin 14 with a current pulse (or voltage pulse) of a second polarity, whereby an upwardly directed force is exerted on the probe 30. For this, a magnetic field generated by the bobbin 14 can be utilized, which magnetic field exerts an attracting force on the annular magnet 34, which force should be sufficiently great to overcome the gravitational force on the probe 30. However, because of the relatively large distance between the bobbin 14 and the annular magnet 34 in the lowest position of the probe 30, the current strength then required is rather great. Therefore, it is preferred that the stop flange 36 is a second, axially polarized annular magnet. The returning of the probe 30 can then be carried out because the magnetic field generated by the bobbin 14 exerts a repulsive force on the second annular magnet 36, which is then located at a relatively short distance from the bobbin 14.

If the second annular magnet 36 is oriented in the same manner as the first annular magnet 34, i.e. with the north pole facing upwards, then the second polarity should be equal to the first polarity. It is true that in that case, when the bobbin 14 is excited with the second pulse, the first annular magnet 34 is repulsed as well, but in the lowest position of the probe 30 the distance from the bobbin 14 to the first annular magnet 34 is greater than the distance from the bobbin 14 to the second annular magnet 36. However, this is not guaranteed under all circumstances. When large eggs are tested, it will even be a rule that in the position of the probe 30 wherein the excitation member 50 touches the egg, the distance from the bobbin 14 to the first annular magnet 34 is less than the distance from the bobbin 14 to the second annular magnet 36. Hence, it is preferred to have the orientation of the second annular magnet 36 be opposite to that of the first annular magnet 34, i.e. with the north pole facing downwards in the example mentioned. The second polarity should then be opposite to the first polarity. In that case, an upwardly directed force is exerted on the two annular magnets 34 and 36, so that the two magnets cooperate to bring the probe 30 back into its rest position again, regardless of the distance through which the probe 30 has been displaced from its rest position.

An additional advantage is then that upon excitation with the first polarity, the two annular magnets 34 cooperate to move the probe downwards, as an addition to the gravitational force, and the downwardly directed force experienced by the probe 30 increases according as the second annular magnet 36 approaches the bobbin 14 and the tube 11, so that also in the case where small eggs are tested, the "travel time" of the probe 30 can be relatively short.

When the probe 30 reaches its rest position, the probe flange 33 contacts the second flange 13. In order to reduce the blow occurring therewith, a shock buffer may be provided in the second flange 13, for instance, and as illustrated, in the form of an O-ring 19.

If an egg is indeed located under the downwards falling probe 30, the excitation member 50 will be arrested by that egg. The probe tube 31 is then also arrested by the magnetic attractive force between the annular magnet 34 and the excitation member 50. The interaction between the egg and the excitation member 50 can be described as a "collision", whereby the eggshell will slightly deform. The eggshell will make a vibrating movement, comparable with the movement of a drumhead, and will touch the excitation member 50 several times, which can be described as a "bouncing" of the excitation member 50. As a result, the excitation member 50 will carry out a vibrating movement, whereby sound vibrations are caused in an air column 20 in the tube 11, above the excitation member 50. These sound vibrations will be propagated upwards in that air column 20 and reach a microphone 40 arranged at the top end of that air column 20.

Owing to the above-mentioned smaller diameter of the top portion of the probe tube 31, the vertical positional freedom of the excitation member 50 is limited. In particular, the excitation member 50 is prevented from touching the microphone 40.

In accordance with an important aspect of the present invention, the microphone 40 in the preferred exemplary embodiment illustrated is not attached to the probe tube 31 but is fixed relative to the subframe 101. In the embodiment shown, this is realized because the housing 10 comprises a cap 21 in the form of an inverted cup, having a cap flange 22 and a bottom 23. The cap flange 22 is mounted on the subframe 101 mentioned, opposite the fastening flange 12. Attached to the bottom 23 of the cap 21 is a vertically downwardly extending support 24 in the form of a hollow bar, whose outside contour preferably corresponds with the inside contour of the probe tube 31. The microphone 40 is attached to the bottom end of that support 24 in any suitable manner, for instance through glueing or clamping. Connecting wires 41, 42 of the microphone 40 extend upwards through the hollow support 24 and can be connected to a data-processing device, as will be understood.

It will be understood that owing to this construction, neither the microphone 40 nor the connecting wires 41, 42 thereof will impede the reciprocation of the probe 30.

The axial length of the cap 21 is such that the stop flange 36 in the rest state illustrated in FIG. 1 remains clear of the bottom 23. Preferably, attached to the cap 21 is a proximity sensor 43 for detecting the probe 30 in its top position or rest position. In the embodiment shown, wherein, in the rest state illustrated in FIG. 1, the stop flange 36 is located very close to the bottom 23 of the cap 21, that proximity sensor 43 is provided in a recess 25 in that bottom 23. Advantageously, the proximity sensor 43 is a Hall sensor, reacting to the second annular magnet 36. Because commercially available Hall sensors are designed so as to be primarily sensitive to the proximity of a south pole, the second annular magnet 36 preferably has its south pole facing upwards.

Via connecting wires 44, the sensor 43 is connected to a control device, not shown, and enables that control device to recognize error situations in time. A first possible error situation occurs when, for whatever reason, the probe 30 does not leave its top position or rest position in response to the bobbin 14 being provided with a current pulse of the first polarity. This error situation is indicated by the sensor 43 to the control device by a signal representative of the proximity of the second annular magnet 36. A second error situation occurs when, for whatever reason, the probe 30 does not regain its top position or rest position in response to the bobbin 14 being provided with a current pulse of the second polarity. This error situation is indicated by the sensor 43 to the control device by a signal representative of the absence of the second annular magnet 36.

As has already been observed, the probe 30 can easily be removed. In that case, the second annular magnet 36 stays behind inside the cap 21, and the second annular magnet 36 will be attracted by the tube 11 and will be retained in that position until the probe 30 or a replacing probe 30 is inserted again. The second annular magnet 36 will automatically resume its proper position on the top end 35 of the probe tube 31. Although the retaining force of the tube 11 is generally sufficient, it is in principle conceivable that the second annular magnet 36 shifts when the probe 30 is taken out, and tilts when the probe 30 is reinserted, so that the second annular magnet 36 will then end up upside down. In order to eliminate this possibility, the axial length of the support 24 is preferably such that the microphone 40 is located at or below the level of the fastening flange 12.

The precise shape of the sound signal received by the microphone 40 depends inter alia on the force with which the excitation member 50 collides with the eggshell. As it is, the egg-testing device 1 is intended to be used in a testing apparatus through which eggs are passed while lying on a conveyor belt or roller conveyor. In general, the eggs lying on that conveyor have a diameter in the range of 34-52 mm, with smaller eggs lying lower in their holders than larger eggs. This means that when a small egg is tested, the distance which the excitation member 50 should travel, while falling, to reach the eggshell is about 24 mm larger than when a large egg is to be tested. A consequence of that larger path to be travelled is that the excitation member 50 reaches a small egg later, and at a greater speed, than when a large egg is being tested.

For realizing measuring signals that are reproducible and can effectively be compared with each other, it is desired that the excitation member 50 reaches each egg at approximately the same speed, while touching the egg approximately according to a center line. For that purpose, in accordance with a further aspect of the present invention, an egg-testing device 1 is preferably individually controlled by a control device 200 which receives information about the diameter of an egg to be examined, and which performs the excitation of the bobbin 14 of that egg-testing device 1 on the basis of this information while taking into account the speed of a conveyor for the eggs, as will be explained hereinbelow with reference to FIGS. 3 and 4.

Figure 4:
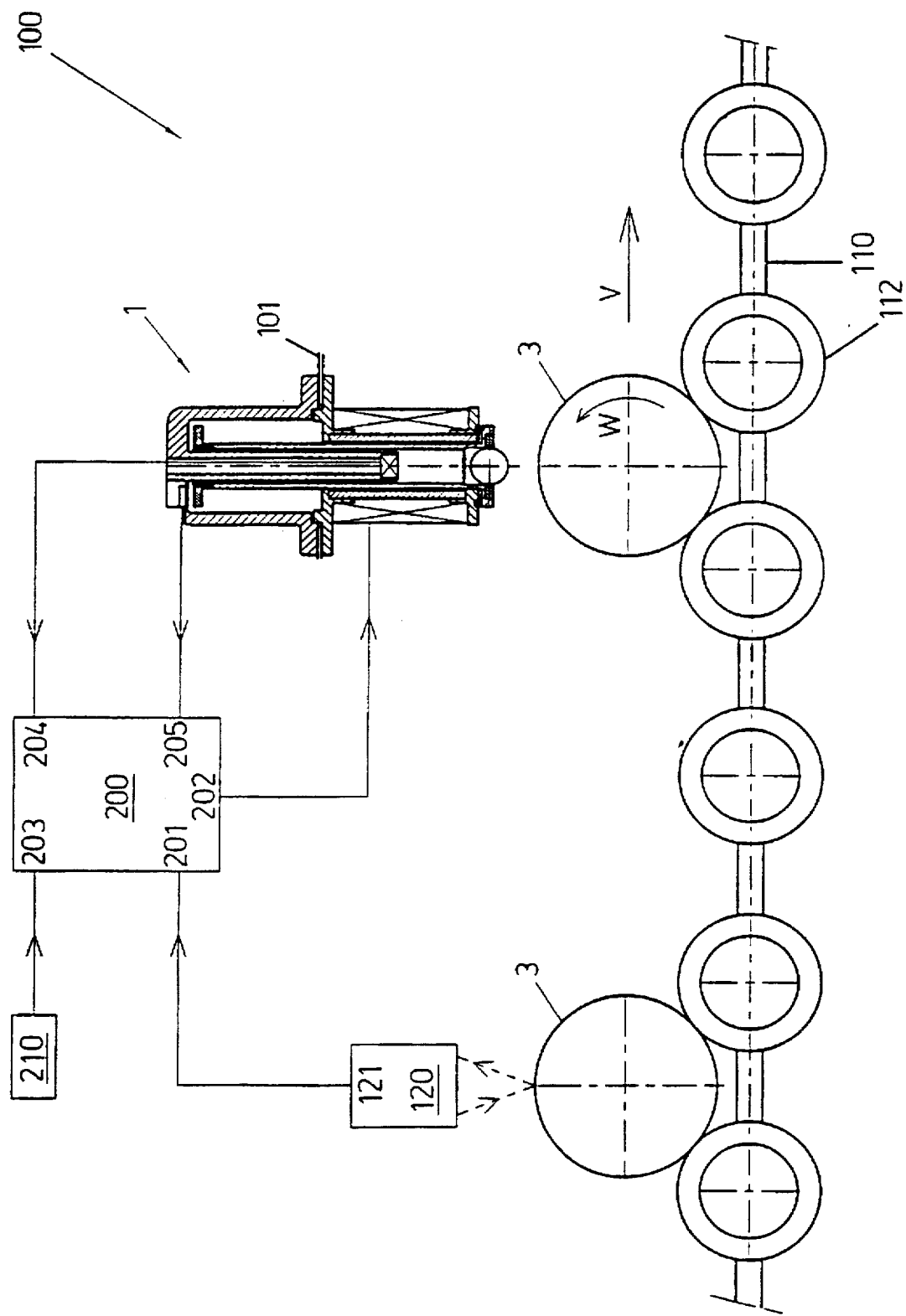
FIG. 4 is a diagrammatic side elevational view of an egg-testing device, with a block diagram of the control thereof.

FIG. 4 diagrammatically shows a side elevation of a testing apparatus 100 with a conveyor 110 for conveying eggs 3 to be examined along an egg-testing device 1 mounted on a subframe of the apparatus 100. Usually, the conveyor 110 is generally a roller conveyor known per se, such as is also described in EP-A-0.602.285. As the nature and construction of the roller conveyor do not constitute a subject of the present invention, and a skilled person need not have knowledge thereof for a proper understanding of the present invention, they will not be further described. It suffices to observe that the eggs 3 are conveyed along the egg-testing device 1 at a predetermined linear speed v, and also rotate at a predetermined angular speed ω about their body axes or center lines 4, which are horizontally directed, perpendicularly to the conveying direction. FIG. 3 is a view in the longitudinal direction of the conveyor 110. Hourglass-like supports 112 mounted on bars 111 carry the eggs 3. FIG. 3 clearly shows that several egg-testing devices 1A, 1B and 1C can be juxtaposed for simultaneously testing one and the same egg 3 independently of one another.

Arranged upstream of the egg-testing device 1 is a diameter-measuring device 120. This measuring device 120 is adapted to generate at its output 121 a signal indicative of the diameter of a passing egg 3. That output 121 is connected to a signal input 201 of the control device 200, an excitation output 202 of which is connected to the wire ends 15, 16 of the bobbin 14.

A skilled person will understand that for the diameter-measuring device 120, any measuring device known per se and suitable for that purpose can be employed. By way of example, reference is here made to an infrared or ultrasonic distance detector, detecting the distance between that detector and a passing egg. As an alternative example, reference is here made to a combination of a light source disposed next to the conveyor and a column of light detectors which is disposed opposite thereto, on the other side of the conveyor, with a passing egg "obscuring" the lowermost light detectors, so that the diameter of that egg determines which light detectors will be obscured and which detectors will continue to receive light. As the nature and construction of the diameter-measuring device do not constitute a subject of the present invention, and a skilled person need not have knowledge thereof for a proper understanding of the present invention, they will not be further described.

The control device 200 is adapted to calculate an amplitude for the excitation current pulse (voltage pulse) for the bobbin 14 of the egg-testing device 1, starting from the signals received from the diameter-measuring device 120. As is already observed hereinabove, this pulse should be great enough to overcome the attractive force between the annular magnet 34 and the tube 11. If the pulse is precisely sufficiently great to overcome this attractive force, the probe 30 falls down at an initial speed $v_0=0$. However, if the pulse has a greater value, extra energy is transferred to the falling probe 30, in the form of kinetic energy, which is equivalent to an initial speed $v_0>0$.

It is known that a freely falling body is at least approximately controlled by the following formulae:

$$v(t)=v_0+g\cdot t \qquad (1)$$

$$s(t)=v_0\cdot t+\tfrac{1}{2}g t^2 \qquad (2)$$

wherein t is the time of fall, g is the acceleration caused by gravity, v(t) is the time of fall at time t, and s(t) is the path travelled at time t.

Hereinbelow, the time passing until the excitation member 50 of the probe 30 contacts the eggshell of an egg 3 will be designated by $t_c$, and the path to be travelled by the probe 30 from the rest position to the eggshell will be designated by $s(t_c)$. The speed at which the excitation member 50 collides with the eggshell will be designated by $v(t_c)$.

For a smaller egg, $s(t_c)$ is greater than for a larger egg. If the probe 30 were in each case excited with the same amplitude, the initial speed $v_0$ would always be the same. From formula (2) it then follows that for a smaller egg $t_c$ is greater than for a larger egg, and from formula (1) it then follows that $v(t_c)$ is greater.

In accordance with the invention, the control device 200 is preferably adapted to calculate the amplitude and/or length of the excitation pulse on the basis of the diameter of the egg 3 in question, i.e. on the basis of $s(t_c)$, in such a manner that the initial speed vo has a magnitude such that $v(t_c)$ is for all eggs substantially equal to a predetermined target value $v_c$.

From the above, it will be understood that the amplitude for the excitation pulse is greater according as the diameter of the egg in question is larger.

The control device 200 is preferably adapted to calculate, starting from the signals received from the diameter-measuring device 120 and taking into account the speed v of the conveyor 110, when the egg 3 in question will precisely be located under the egg-testing device 1, i.e. the point of time t1 when the center line 4 of the egg 3 in question intersects the center line 2 of the probe 30, and to excite the bobbin 14 of the egg-testing device 1 at the point of time t1−$t_c$.

In this connection, it is observed that the control device 200 preferably comprises an input 203 for receiving instructions, for instance via a keyboard 210. This permits attending personnel to give the control device 200 instructions about the desired force with which the excitation member 50 excites the eggs 3, i.e. instructions about $v_c$. In this manner, it is possible to optimally adapt the egg-testing device 1 to different types of eggs: for instance, eggs that are known to have weak, thin shells can be excited "gently".

The control device 200 is provided with a signal input 204 coupled to the microphone 40, enabling the control device 200 to detect the exact point of time of excitation. After the passage of a predetermined time after this excitation time, the control device 200 excites the bobbin 14 again, but now with a pulse of opposite polarity, to promptly return the probe 30 to the rest position. To enable checking whether the probe 30 actually reaches the rest position, a signal input 205 of the control device 200 is coupled to the proximity sensor 43. In a practical embodiment, the second pulse is generated directly after excitation: the entire system has such a slowness, inter alia because the magnetic field has to be built up in the bobbin 14, that it automatically involves waiting for the above-mentioned predetermined time.

The egg 3 is now tested at one location, and the testing procedure took about 100–120 ms.

In general, it is desired to test each egg 3 at several locations along its circumference, measured according to the direction of rotation ω. In practice, several egg-testing devices 1 are used for that purpose, which devices are arranged one behind the other in the conveying direction, the distance in between being chosen in relation to the conveying speed v and the rotational speed ω. When it is for instance desired to test the eggs 3 at four positions, spaced apart 90°, four egg-testing devices 1, disposed one behind the other, are needed therefor.

In accordance with a further aspect of the present invention, each egg 3 is tested several times in succession by means of each egg-testing device 1. To that end, after the lapse of a predetermined wait time $t_w$, after the above-described testing procedure has ended, preferably about 30 ms, the bobbin 14 is re-excited with the first polarity, as a result of which the above testing procedure repeats itself. In the meantime, the egg 3 on the roller conveyor 110 has rotated through an angle α which is determined by, on the one hand, the rotational speed ω and, on the other, the duration $t_p$ of the above-described testing procedure, increased by the above predetermined time $t_w$, according to the formula α=ω·($t_p$+$t_w$).

Meanwhile, the egg 3 has also been displaced by the conveyor 110 through a horizontal distance A determined by, on the one hand, the conveying speed v and, on the other, the duration $t_p$ of the above-described testing procedure, increased by the above predetermined time $t_w$, according to the formula A=v·($t_p$+$t_w$). In order to ensure that the egg 3 is struck by the excitation member 50 at a central position all the same, i.e. substantially perpendicularly to the surface of the eggshell, the egg-testing apparatus 100 according to the invention preferably has a subframe 101 which moves along with the conveyor 110. It is possible that the subframe 101 is displaced relative to a main frame, not shown, at a speed equal to the conveying speed v and, after two or more excitations, is placed back linearly, preferably at greater speed. However, it is also possible that the subframe 101 can pivot relative to the main frame about a horizontal axis which is perpendicular to the conveying direction, and which preferably intersects the center line 2 of the probe 30. Accordingly, the egg-testing device 1 makes a reciprocating swinging movement about that pivot.

Figure 5A:
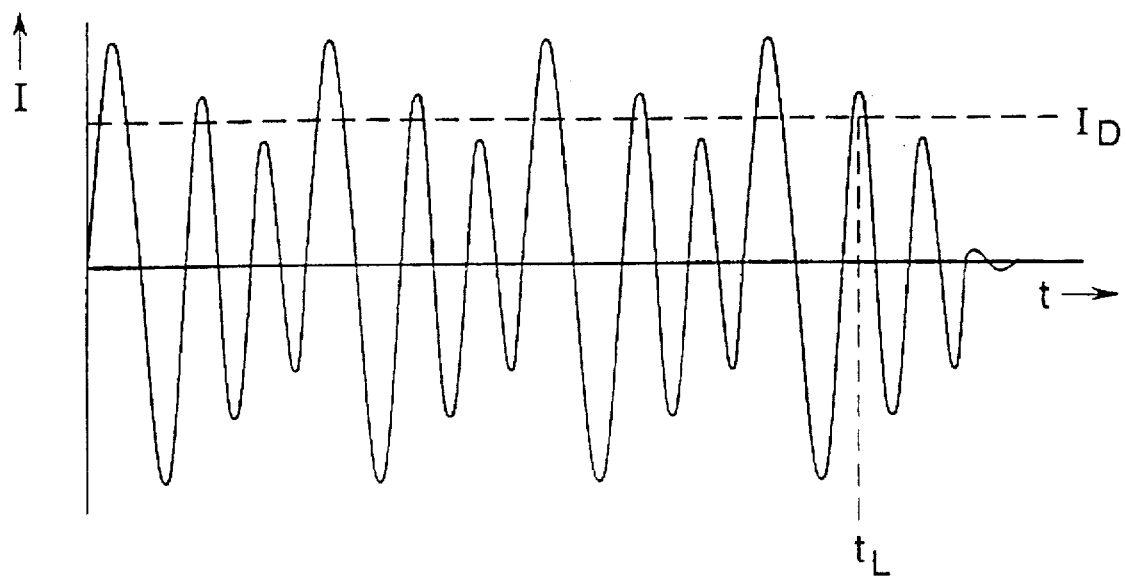
FIGS. 5A and 5B illustrate the signal processing according to the invention.
Figure 5B:
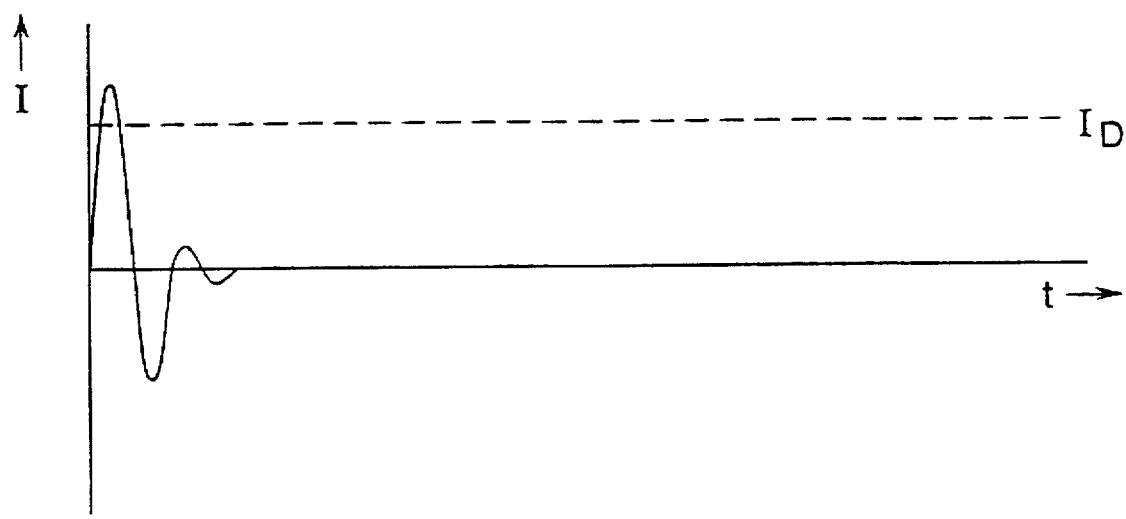

FIG. 5A is illustrative of the signal provided by the microphone 40 during the testing of a "good" egg, while FIG. 5B is illustrative of the signal provided by the microphone 40 during the testing of a "bad" egg, such as a cracked egg. Plotted along the horizontal axis is the time; the length of the time axis shown corresponds to about 25 ms. Plotted along the vertical axis in arbitrary units is the intensity I of the measuring signal. The measuring signal can be characterized as a sinusoidal signal of decreasing amplitude. The maximum amplitude corresponds to a "collision" between the egg and the excitation member 50. In the illustration of FIG. 5A, four successive ones of such "collisions" can be recognized.

In the case of a cracked egg, the measuring signal can be characterized as a sinusoidal signal of a very rapidly decreasing amplitude, usually more rapidly than in the case of a good egg. Further, the number of times that the maximum amplitude occurs will be less: in the illustration of FIG. 5B, the maximum amplitude occurs only once.

In accordance with the invention, the measuring signal is examined in two manners. In the first place, the measuring signal is compared with a predetermined threshold value $I_D$. That threshold value $I_D$ may be settable, and inputted by attending personnel. It is possible that the absolute value of the measuring signal is compared with the threshold value $I_D$.

Then, it is counted how often the measuring signal exceeds the threshold value $I_D$. In the illustration of FIG. 5A, this is 8 times. In a practical experiment, the measuring signal had a higher frequency than is sketched, and the counting value N for a good egg had a value in the range of from 10 to 20. In the case of a cracked egg, the counting value N is much lower: in the illustration of FIG. 5B, this is 1 time, but in practice, the counting value may still increase to about 5. In accordance with an aspect of the present invention, the counting value N is therefore compared with a predetermined threshold value $N_{min}$. If the condition $N > N_{min}$ is met, then the egg is approved by the testing apparatus 100. The threshold value $N_{min}$ mentioned can likewise be settable and inputted by attending personnel.

However, in practice, it has appeared that situations may occur in which a good egg provides a measuring signal whose amplitude decreases very rapidly, as is sketched in FIG. 5B for a cracked egg, but for which the maximum amplitude nevertheless occurs just as often as in the case of a "normal" egg, i.e. four times in the example of FIG. 5A. In such a case, the counting value N can for instance be equal to 4, as a consequence of which the egg in question will be disapproved wrongly, on the basis of the above-mentioned criterion.

In accordance with a further aspect of the present invention, a solution to this problem is provided in that it is also monitored at which point of time (calculated from the first peak, or calculated from the excitation pulse of the first polarity provided by the control device 200) the measuring signal exceeds the threshold value $I_D$, and the time $t_L$ associated with the last time that this happens is compared with a predetermined threshold value $t_{min}$. If the condition $t_L > t_{min}$ is met, then the egg is approved by the testing apparatus 100. The threshold value $t_{min}$ can also be settable and inputted by attending personnel. In the illustration of FIG. 5A, $t_L$ is about 20 ms; a suitable value for $t_{min}$ is, for instance, 15 ms.

In this manner, according to this aspect of the present invention, eggs are prevented from being disapproved wrongly. In fact, the latter method for judging the measuring signals is in itself sufficient for distinguishing good eggs from cracked eggs; with the former method it is also possible to make an observation about the size of a crack, if any.

In this connection, it is noted that it is not necessary to actually express the time in ms. If it is sufficient to use a quantity representative of that time: for this purpose, clock pulses can for instance be counted. In an illustrative embodiment, by the excitation pulse provided by the control device 200, a counter controlled by a clock generator is also reset, and each time when the measuring signal exceeds the threshold value $I_D$, the counter reading is copied in a memory register. Accordingly, when the control device 200 generates the second excitation pulse in order to return the probe 30 to its rest position, to indicate that the measurement is over, the memory register can be read out.

It will be understood by a skilled person that it is possible to change or modify the embodiment shown of the device according to the invention, without departing from the inventive concept or the scope of protection. For instance, it is possible that the excitation member 50 is magnetic, and that the tube 11 is magnetic. It is also possible that the annular magnet 34 is replaced by a number of magnetic bars, disposed along the circumference of the probe tube 31, adjacent the bottom end 32 thereof. Also, the choice of the materials used is not critical, as long as they are resistant to egg contents and the like without rusting.

Further, the examination of the measuring signal can be carried out by the control device 200 or by a separate signal-processing device.

I claim:

1. A probe for testing an egg, comprising:
   a hollow, tubular probe body;
   an excitation member disposed adjacent a first end of the probe body; and
   retaining means comprising a magnetic field for retaining the excitation member relative to the probe body in such a manner that the excitation member is free to carry out a vibrating movement in a direction parallel to a center line of the probe body.

2. A probe according to claim 1, wherein the excitation member is contactlessly retained by the magnetic field.

3. A probe according to claim 1, wherein the retaining means comprise at least one permanent magnet.

4. A probe according to claim 3, wherein the retaining means comprise a ring magnet disposed adjacent a first end of the probe body, and wherein the excitation member comprises a magnetically attractable material.

5. A probe according to claim 4, wherein the excitation member is spherical.

6. An egg-testing device, comprising:
   a probe including
   (1) a hollow, tubular probe body,
   (2) an excitation member disposed adjacent a first end of the probe body, and
   (3) retaining means comprising a magnetic field for retaining the excitation member relative to the probe body in such a manner that the excitation member is free to carry out a vibrating movement in a direction parallel to a center line of the probe body;
   a microphone adapted to receive sound waves generated by the excitation member in an air column within the probe body; and
   a housing, the probe being bearing-mounted in said housing so as to be axially displaceable, the microphone being fixedly mounted relative to said housing.

7. An egg-testing device according to claim 6, wherein the microphone is attached to an end of an elongated hollow support extending into the interior of the hollow probe body.

8. An egg-testing device according to claim 7, wherein the elongated hollow support is attached to a cap comprising means for attachment to a subframe.

9. An egg-testing device according to claim 6, wherein the housing comprises:
   a hollow metal tube for guiding the probe,
   comprising a fastening flange for attachment to a subframe, and comprising a bobbin provided around said tube.

10. An egg-testing device according to claim 6, wherein on a second end of the probe tube a stop flange is formed for defining a lowest extreme position of the probe.

11. An egg-testing device according to claim 10, wherein the stop flange is formed by a second annular magnet.

12. An egg-testing device according to claim 6, comprising a sensor for detecting the position of the probe relative to the housing.

13. An egg-testing device according to claim 12, wherein the sensor comprises a proximity sensor.

14. A testing apparatus for testing eggs, including:
   at least one egg-testing device comprising
   a probe including
   (1) hollow, tubular probe body,
   (2) an excitation member disposed adjacent a first end of the probe body, and
   (3) retaining means comprising a magnetic field for retaining the excitation member relative to the probe body in such a manner that the excitation member is free to carry out a vibrating movement in a direction parallel to a center line of the probe body;
   a microphone adapted to receive sound waves generated by the excitation member in an air column within the probe body; and
   a housing, the probe being bearing-mounted in said housing so as to be axially displaceable, the microphone being fixedly mounted relative to said housing and having a diameter-measuring device adapted to generate, at an output thereof, a signal indicative of the diameter of an egg.

15. A testing apparatus according to claim 14, comprising a control device of which a signal input is connected to the output of the diameter-measuring device, and of which an excitation output is connected to the bobbin, said control device being adapted to control each egg-testing device individually on the basis of the signals received at its input.

16. A testing apparatus according to claim 15, wherein the control device is adapted to set at least one of amplitude and length of an excitation pulse for each bobbin so that the excitation member reaches each egg at a speed substantially equal to a predetermined target value.

17. A testing apparatus according to claim 15, comprising a conveyor for conveying eggs to be examined along the egg-testing devices, the control device being adapted to excite the bobbin on a basis of diameter of the eggs to be examined and taking into account speed of the conveyor.

18. A testing apparatus according to claim 15, wherein the control device is adapted to set timing of an excitation pulse for each bobbin so that the excitation member strikes each egg when a center line of said egg substantially intersects a center line of the probe.

19. A testing apparatus according to claim 15, wherein the control device is adapted to re-excite each bobbin after a predetermined wait time in order to test an egg at least twice by means of the same egg-testing device.

20. A testing apparatus according to claim 19, further comprising a subframe movable along with the conveyor for attachment of the egg-testing devices.

21. A testing apparatus according to claim 20, wherein the subframe is pivotable about a horizontal axis perpendicular to the conveying direction.

22. A method for examining an egg for the presence of ruptures and cracks, comprising the steps of:
  providing a measuring signal by means of a probe including
   (1) a hollow, tubular probe body,
   (2) an excitation member disposed adjacent a first end of the probe body, and
   (3) retaining means comprising a magnetic field for retaining the excitation member relative to the probe body in such a manner that the excitation member is free to carry out a vibrating movement in a direction parallel to a center line of the probe body;
  comparing the measuring signal with a predetermined threshold value;
  counting how often the measuring signal exceeds the threshold value;
  comparing the count value with a predetermined threshold value; and
  approving the egg if the count value exceeds the predetermined threshold value.

23. A method for examining an egg for the presence of ruptures and cracks, comprising the steps of:
  providing a measuring signal by means of a probe including
   (1) a hollow, tubular probe body,
   (2) an excitation member disposed adjacent a first end of the probe body, and
   (3) retaining means comprising a magnetic field for retaining the excitation member relative to the probe body in such a manner that the excitation member is free to carry out a vibrating movement in a direction parallel to a center line of the probe body;
  comparing the measuring signal with a predetermined threshold value;
  comparing a point of time, associated with the last time that the measuring signal exceeds said threshold value, with a predetermined threshold value; and
  approving the egg if the point of time is greater than the predetermined threshold value.

* * * * *